United States Patent
Plaian et al.

(10) Patent No.: US 10,070,786 B2
(45) Date of Patent: Sep. 11, 2018

(54) SCANNING PERIMETER

(71) Applicant: CENTERVUE S.P.A., Padua (IT)

(72) Inventors: Andrei Plaian, Ponte San Nicolò (IT); Federico Manzan, San Pietro di Feletto (IT); Marco D'Aguanno, Padua (IT); Irene Mogentale, Due Carrare (IT)

(73) Assignee: Centervue S.p.A., Padua (IT)

( * ) Notice: Subject to any disclaimer, the term of this patent is extended or adjusted under 35 U.S.C. 154(b) by 32 days.

(21) Appl. No.: 15/510,009

(22) PCT Filed: Sep. 7, 2015

(86) PCT No.: PCT/EP2015/070404
§ 371 (c)(1),
(2) Date: Mar. 9, 2017

(87) PCT Pub. No.: WO2016/037986
PCT Pub. Date: Mar. 17, 2016

(65) Prior Publication Data
US 2017/0251919 A1     Sep. 7, 2017

(30) Foreign Application Priority Data
Sep. 12, 2014   (IT) .............................. TV2014A0132

(51) Int. Cl.
*A61B 3/14*   (2006.01)
*A61B 3/12*   (2006.01)
(Continued)

(52) U.S. Cl.
CPC ............ *A61B 3/145* (2013.01); *A61B 3/0025* (2013.01); *A61B 3/0091* (2013.01); *A61B 3/024* (2013.01);
(Continued)

(58) Field of Classification Search
CPC ......... A61B 3/145; A61B 3/024; A61B 3/156; A61B 3/1025; A61B 3/0091; A61B 3/12; A61B 3/0025; G02B 26/105
(Continued)

(56) References Cited

U.S. PATENT DOCUMENTS 4,279,478 A   7/1981 Matsumura
5,046,835 A   9/1991 Billeter et al.
(Continued)

FOREIGN PATENT DOCUMENTS

CN   102265310 A   11/2011
CN   103815866 A   5/2014
(Continued)

OTHER PUBLICATIONS

Chinese Patent Office: Office Action dated Feb. 23, 2018 in Application No. 201580061449.1.
(Continued)

*Primary Examiner* — Tuyen Tra
(74) *Attorney, Agent, or Firm* — Patterson Intellectual Property Law, P.C.; Gary L. Montle

(57) ABSTRACT

A scanning perimeter as disclosed herein comprises a first projection means projecting a first projection beam to uniformly illuminate a portion of a retina, said first projection beam passing through the pupil of the eye at a second separation region between a first crossing region, at which said illumination beam passes through the pupil, and a second crossing region of the pupil, at which light reflected by the retina passes through the pupil. A second projection means projects a second projection beam to project at least a fixation target on the retina, said second projection beam passing through the pupil at said first crossing region or said second crossing region. A third projection means projects a third projection beam to project at least a light stimulus on
(Continued)

the retina, said third projection beam passing through the pupil at said first crossing region or said second crossing region.

22 Claims, 6 Drawing Sheets

(51) Int. Cl.
  *A61B 3/00* (2006.01)
  *A61B 3/10* (2006.01)
  *G02B 26/10* (2006.01)
  *A61B 3/15* (2006.01)
  *A61B 3/024* (2006.01)

(52) U.S. Cl.
  CPC .............. *A61B 3/1025* (2013.01); *A61B 3/12* (2013.01); *A61B 3/156* (2013.01); *G02B 26/105* (2013.01)

(58) Field of Classification Search
  USPC ........................................ 351/200, 205, 206
  See application file for complete search history.

(56) References Cited

U.S. PATENT DOCUMENTS 7,828,437 B2 * 11/2010 Kikawa ................. A61B 3/102
                                                                  351/200
8,657,446 B2    2/2014 Weleber et al.

FOREIGN PATENT DOCUMENTS

JP      2010233978 A    10/2010
WO      2010113193 A1   10/2010

OTHER PUBLICATIONS

European Patent Office: International Search Report for PCT/EP2015/070404 dated Nov. 23, 2015 (dated Oct. 12, 2015).

* cited by examiner

SCANNING PERIMETER

BACKGROUND OF THE INVENTION

The present invention relates to the field of eye examination apparatus, in particular apparatus for measuring the visual function of the eye.

In the field of ophthalmology, the perimetry technique is known for measuring the visual function of the eye. According to this methodology, the patient is shown with light stimuli of various shape and intensity located in selectable positions of the field of view and superimposed on a light background of uniform intensity.

During the examination, the patient looks toward a light fixation target, so as to hold the eye still, and indicates whether he/she sees the light stimuli projected.

In this way, it is possible to determine the minimum threshold of light intensity that the patient's eye is still able to see in various different points of the field of view.

This allows tracing a map of the visual sensitivity of the eye to be used for medical diagnosis.

Numerous examples are known of eye examination apparatus, commonly known with the term "perimeter" and which allow implementation of the perimetry technique for measuring visual function, as described above.

Some of these apparatus comprise a system for projecting a uniform light background on the retina and a system for projecting visible stimuli that can be selectively positioned inside the field of view of the eye.

In some prior art perimeters, these projection systems are operatively associated with a system that allows images of the retina to be acquired.

Apparatus of this type are characterized by high precision in positioning of the light stimuli, given that, in calculating the position of these latter, it is possible to compensate for any movements of the patient's eye.

Moreover, in addition to the result of the perimetry test, these apparatus are capable of providing images of the eye fundus. This is often useful for medical diagnosis.

Examples of perimeters capable of acquiring images of the retina are described in the patent documents U.S. Pat. No. 6,705,726, U.S. Pat. No. 7,690,791 and WO2010113193.

U.S. Pat. No. 7,690,791 describes a combination between a confocal system for acquiring images of the retina and a display that can be positioned in front of the patient's eye. Light stimuli that can be selectively positioned in the field of view are projected on the display.

The document does not provide practical solutions for producing optical integration between the aforesaid display and the confocal acquisition system along a common optical path directed toward the patient's eye.

U.S. Pat. No. 6,705,726 describes the combination between an image acquisition system of the retina and an LCD display capable of showing the patient a uniform light background, a fixation target and light stimuli to test visual function of the eye or perform other tests.

The image acquisition system (which in this case is not of confocal type) illuminates the patient's retina with infrared light and records video of the same retina.

It has been seen that this acquisition system often provides low contrast infrared images, of little use for medical diagnosis and difficult to use to detect eye movements in real time.

The use of a LCD display to project the light stimuli has some disadvantages. The most important of these are:

- low precision of the intensity of the light stimuli: light stimuli projected from different regions of the surface of the display, which can have different characteristics from one another;
- low interval of variation (dynamic range) of the intensity of the light stimuli: in general it is possible to obtain a variation of around 30 dB between a minimum and maximum intensity of the light stimuli projected (with other solutions that do not use liquid crystals it is possible to reach intervals of variation of around 50 dB);
- discrete form of the light stimuli: the light stimuli projected are typically composed of a few pixels;
- variations in the light intensity on the surface of the stimulus (light regions at the surface of the pixel and dark regions at the boundaries between adjacent pixels);
- variation of intensity of the light stimuli with the temperature of the LCD display.

Patent application WO2010/113193 describes a scanning perimeter comprising an acquisition system of images of the retina of confocal line scanning type, which uses infrared light to illuminate the retina. This acquisition system is operatively associated with a projection assembly, coupled with the optical path of the machine by means of a cold mirror. The projection assembly comprises optical elements that separately produce a fixation target, a uniform light background and light stimuli to measure the sensitivity of the retina.

The apparatus described in this patent document has considerable disadvantages in terms of structural complexity and costs for its production on an industrial scale.

As well as the line scanning acquisition system, this apparatus comprises a projection assembly that, among other things, provides for the use of a plurality of emitters, two beam splitters, a cold mirror, at least two lenses and a two-way electromechanical system for movement of a mirror that modifies the position of the visual stimulus projected on the retina.

To project a uniform light background, the aforesaid scanning perimeter uses a light surface optically conjugated with the retina, which generates light with uniform intensity.

This solution is generally costly, given that the uniformity of the light background generated depends substantially on the quality of the components used.

Moreover, the light background projected can have non-uniform regions due to dirt that can deposit on the aforesaid projection surface, which would be visible to the patient in the form of dark marks with well-defined outlines.

BRIEF SUMMARY OF THE INVENTION

The main aim of the present invention is to provide a scanning perimeter which allows the problems of the prior art, indicated above, to be solved.

Within this aim, an object of the present invention is to provide a multifunctional scanning perimeter, capable of performing perimetry tests and of acquiring images of the retina.

A further object of the present invention is to provide a scanning perimeter that allows different types of visual function tests to be performed, including a perimetry test with white light stimuli on a white background and a perimetry test with blue light stimuli on a yellow background.

A further object of the present invention is to provide a scanning perimeter with some automatic functions, for example acquiring images of the retina with automatic adjustment of the light exposure.

A further object of the present invention is to provide a scanning perimeter capable of performing more precise measurements of the visual function of the eye, for example through real-time compensation of the movements of the eye examined.

A further object of the present invention is to provide a scanning perimeter that is easy to produce on an industrial scale, at competitive costs.

This aim and these objects, together with other objects that will be more apparent from the subsequent description and from the accompanying drawings, are achieved according to the invention, by a perimeter according to claim 1 and to the related dependent claims appended below.

BRIEF DESCRIPTION OF THE SEVERAL VIEWS OF THE DRAWINGS

Further characteristics and advantages of the eye examination apparatus according to the invention will be more apparent with reference to the description given below and to the accompanying figures, provided purely for explanatory and non-limiting purposes, wherein.

DETAILED DESCRIPTION OF THE INVENTION

Figure 1:
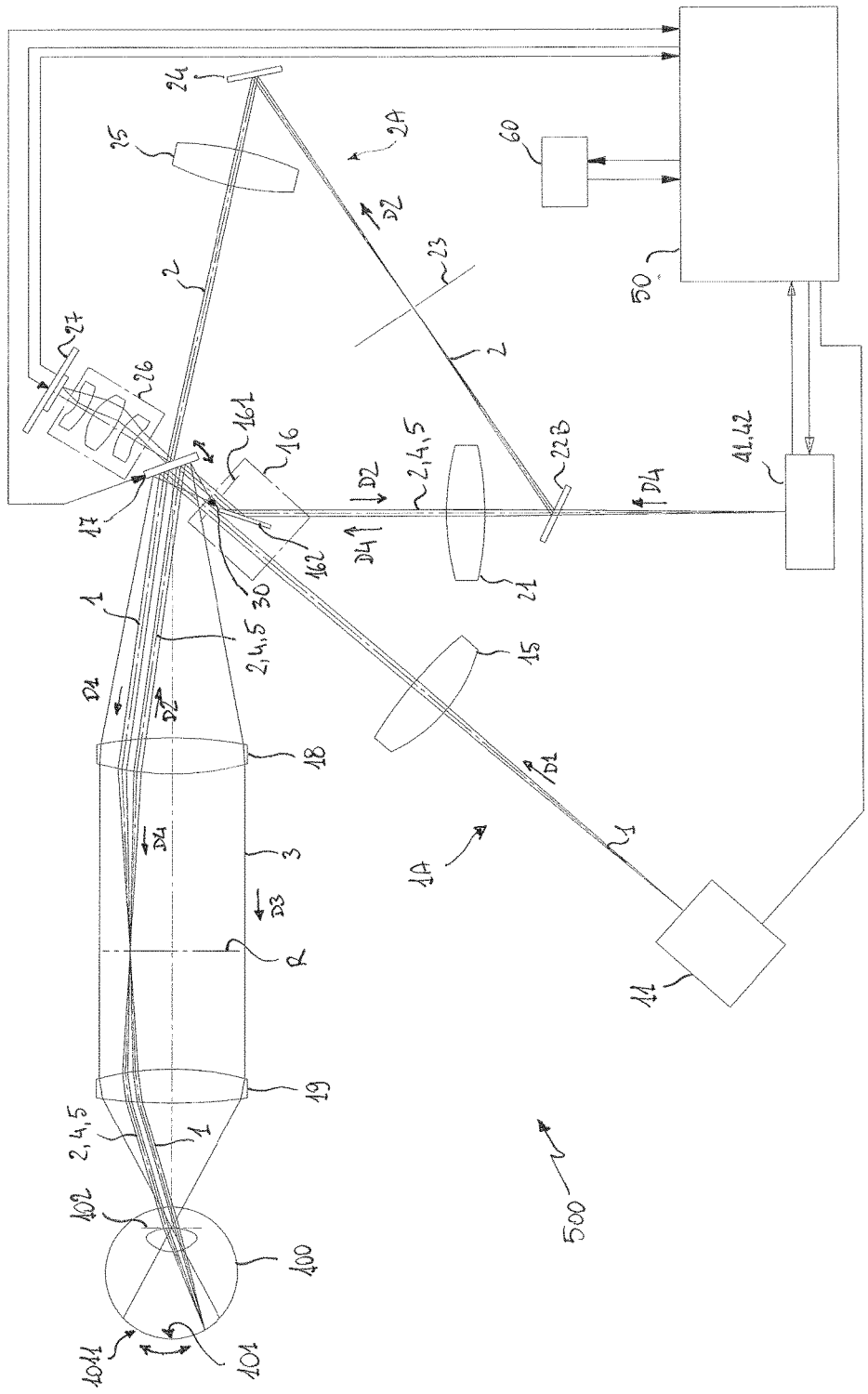
FIG. 1 schematically shows the scanning perimeter according to the invention, in an embodiment thereof.

With reference to FIG. 1, the present invention relates to a scanning perimeter 500.

The perimeter 500 comprises an illuminator 11 comprising at least a light source.

The perimeter 500 comprises an optical illumination path 1A, along which an illumination beam 1, projected by the illuminator 11, reaches the retina 101 of the eye 100.

During the operation of the perimeter 500, the optical path 1A therefore extends from the illuminator 11 to the retina 101.

Preferably, the illuminator 11 is arranged to project toward the retina a light beam 1 intended to illuminate, during the operation of the perimeter 500, a portion of retina having the shape of a line of light that extends along a main axis of extension.

Figure 2:
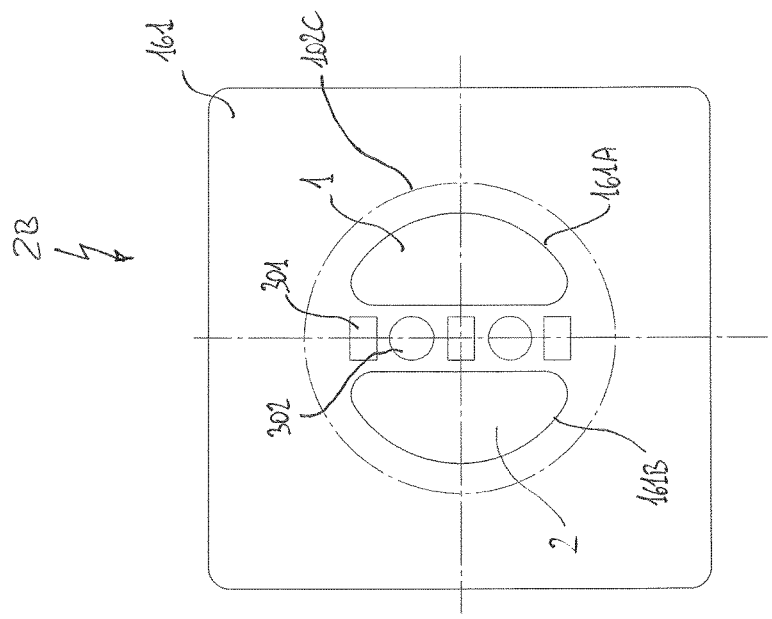
FIGS. 2-5 schematically show some details of the scanning perimeter of FIG. 1.
Figure 2:
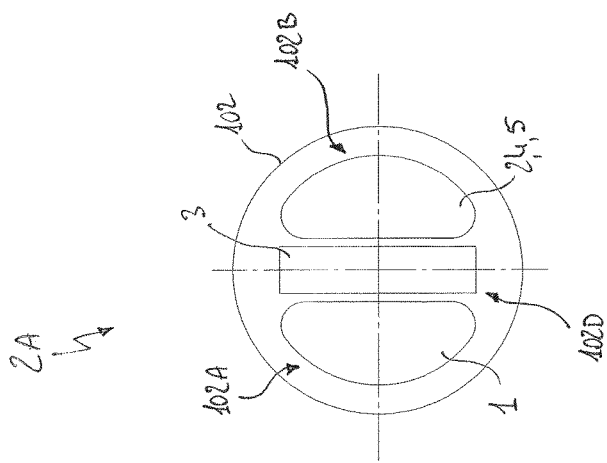

The illumination beam 1 passes through the pupil 102 of the eye at a first crossing region 102A (FIG. 2, view 2A).

The perimeter 500 comprises acquisition means 27 adapted to receive a beam 2 of light reflected by the retina 101 and to acquire one or more images of the same retina.

The perimeter 500 comprises an optical acquisition path (or optical imaging path) 2A, along which the light 2 reflected by the retina 101 reaches the acquisition means 27.

During the operation of the perimeter 500, the optical path 2A therefore extends from the retina 101 to the acquisition means 27.

The perimeter 500 comprises scanning means 17 adapted to cyclically perform optical scans of the retina 101.

Each optical scan is performed by moving, along a scanning direction DS (FIG. 3) and with period TS, the illumination beam 1 projected by the illuminator 11 on the surface of the retina 101.

Through the scanning means 17, the line of light projected by the illuminator is moved periodically, during the optical scans, along the surface of the retina according to the scanning direction DS.

Preferably, the scanning means 17 also have the function of directing at least a portion of the light 2 reflected by the retina along the optical path 2A toward the acquisition means 27.

The perimeter 500 comprises separation means of the light beams 16 adapted to separate the illumination beam 1 from light 2 reflected by this latter.

In particular, the separation means of the light beams 16 are adapted to create, at the level of the pupil 102 of the eye and of the surfaces optically conjugated with this latter, a separation region 102D between the illumination beam 1 and the beam 2 of light reflected by the retina and used by the acquisition means 27 to acquire images.

The illuminator 11, the separation means of the light beams 16 and the scanning means 17 are advantageously arranged in series along the optical path 1A (with reference to the direction D1 of the illumination beam 1).

Preferably, the perimeter 500 comprises a first optics 15 arranged along the optical path 1A between the illuminator 11 and the separation means 16 of the beams.

Preferably, the perimeter 500 comprises a scanning optics 18 and an eyepiece 19, arranged downstream of the scanning means 17 (with reference to the direction of travel D1 of the illumination beam 1) along the optical path 1A so as to be passed through by the illumination light 1.

The scanning means 17, the separation means of the light beams 16 and the acquisition means 27 are advantageously arranged in series along the optical path 2A (with reference to the direction of travel D2 of the light beam 2).

Also the eyepiece 19 and the scanning optics 18 are arranged along the optical path 2A passed through by the reflected light 2, before this latter reaches the scanning means 17.

Preferably, the perimeter 500 comprises a confocal diaphragm 23 arranged along the optical path 2A so as to be optically conjugated with the retina 101, during the operation of the perimeter 500.

For greater clarity of exposition, it is specified that, within the scope of the present invention, the definition "optically conjugated" identifies positioning in the exact position of optical conjugation or in a relatively small neighbourhood (with respect to the lengths of the optical paths of the perimeter 500) of the exact position of optical conjugation.

The confocal diaphragm 23 preferably comprises at least a confocal opening 231 that allows the passage of a portion of the reflected light 2 and is capable of at least partially stopping the light reflected by some surfaces of the perimeter 500 or of the eye 100 that are not optically conjugated with the retina.

Preferably, the perimeter 500 also comprises a second optics 21, the mirror 22A or a beam splitter 22B, a third optics 25, an objective 26 arranged along the optical path 2A, between the scanning means 17 and the acquisition means 27.

Other construction variants that provide for the use of mirrors or diaphragms having configurations different from the one shown in the aforesaid figures are possible.

Preferably, the illuminator 11 comprises at least a first light source consisting of an LED (Light Emitting Diode).

Preferably, the acquisition means 27 consist of, for example, CCD or C-MOS sensors of a digital video camera. They receive the light 2 at a receiving surface and advantageously allow the retina 101 to be observed and filmed.

Preferably, the separation means of the light beams 16 comprise a separation diaphragm 161, optically conjugated with the pupil 102 during the operation of the perimeter 500.

Preferably, the separation means of the light beams 16 comprise a mirror 162 adapted to divert the reflected light 2 directed by the scanning means 17 along the acquisition path 2A.

Preferably, the separation diaphragm 161 comprises shaped openings 161A, 161B for passage of the illumination beam 1 and of light reflected by the retina, respectively.

Preferably, the scanning means 17 perform periodic scanning movements that cyclically move the direction of reflection of the illumination beam between two end positions (hereinafter end-of-travel positions).

Preferably, the scanning means 17 comprise a resonant mirror oscillating around a rotation axis.

Preferably, the mirror 17 comprises two opposed reflecting surfaces.

Other constructive solutions that, for example, provide for the use of a polygonal mirror, an array of micromirrors and the like, are possible.

For greater clarity of exposition, it should be specified that the scanning means 17 can also operate (i.e. perform periodic scanning movements between the aforesaid end-of-travel positions) when the illuminator 11 is deactivated, i.e. does not project light toward the retina 101.

When the scanning means 17 and the illuminator 11 are activated, the scanning means 17 perform one or more optical scans of the retina 101 moving the beam of light 1 (preferably substantially in the shape of a line of light) projected on the surface of the retina 101 along a scanning direction DS.

The general operation of the perimeter 500, with regard to the acquisition of images of the retina 101, is now described in further detail.

The illumination beam 1 projected by the illuminator 11 passes through the optics 15 and the separation means 16 of the light beams, in particular at the opening 161A of the separation diaphragm 161.

The illumination beam 1 is scanned by the scanning means 17 that direct it toward the retina 101 moving around the rotation axis thereof. It passes through the scanning optics 18 and the eyepiece 19 and enters the eye 100 to illuminate the retina 101.

To enter the eye, the illumination beam 1 passes through the pupil 102 at the first crossing region 102A (FIG. 2, view 3A).

On the retina 101, the illuminated region consists of the light image projected by the illuminator 11. This illuminated region, preferably in the shape of a line of light, moves along the retina according to the scanning direction DS set by the scanning means 17. The scanning direction DS is substantially perpendicular to the main axis of extension of this line of light.

The light reflected by the retina 101, illuminated by the beam 1, exits from the eye through the pupil 102.

The light reflected by the retina is de-scanned by the scanning means 17 that direct it along the optical path 2A.

The light reflected by the retina passes through the separation means 16 of the light beams, in particular through the opening 161B of the separation diaphragm 161. This opening selects (from the light reflected by the retina that reaches the separation diaphragm 161) the beam 2 of light reflected by the retina and directed toward the acquisition means 27 and used by these latter to acquire the images of the retina.

The separation means 16 of the light beams (in particular the separation diaphragm 161 and the related opening 161B) define, at the pupil 102, during the operation of the scanning perimeter, a second crossing region 102B, at which the beam 2 of light reflected by the retina and used by the acquisition means 27 to acquire images of the retina passes through the pupil (FIG. 2, view 2A).

The separation region 102D is located between the crossing regions 120A, 102B.

The configuration of the crossing regions 102A, 102B and of the separation region 102D must not be intended as limited to the one shown in FIG. 2, view 2A.

Other solutions are possible, according to which some or all of the regions 102A, 102B and 102D are divided into separate portions or have different shapes with respect to those shown in FIG. 2, view 2A.

For example, a possible solution could provide for the existence of a single central crossing region 102A and a crossing region 102B divided into two portions located on one and on the other side of the region 102A. In this case, the separation region 102D would also be divided into two lateral portions, each of which located between the central crossing region 102A and a corresponding lateral portion of the crossing region 102B.

Another example could comprise a crossing region 102B in the shape of a central disc, surrounded by a separation region 102D of annular shape and by a crossing region 102A, in turn annular, positioned outside the separation region 102D.

The separation of the light beams 1, 2 at the level of the pupil 102 greatly reduces the probability that undesired reflections of the illumination light 1, which come from surfaces of the eye other than the retina, reach the acquisition means 27.

The light beam 2, selected by the separation means 16, passes through the optics 21, is reflected by the mirror 22, passes through the confocal diaphragm 23, is reflected by the mirror 24 and passes through the optics 25.

The passage of the light beam 2 through the confocal diaphragm 23 greatly reduces the probability that undesired reflections, which come from objects positioned in planes different from the retina 101 or optically conjugated with the same retina, reach the acquisition means 27.

The light beam 2 is once again scanned by the scanning means 17 and directed toward the acquisition means 27.

The light beam 2 passes through the objective 26 to reach the acquisition means 27 that acquire one or more images of the retina 101.

Further variants of embodiment are possible with regard to the acquisition system of the images of the retina.

For example, the acquisition means 27 could comprise a linear sensor and be positioned in place of the confocal diaphragm 23.

The perimeter 500 also comprises a control unit 50 to control the operation of the same perimeter, for example to perform signal acquisition, data storage, data calculation and control signal generation functions.

Preferably, the control unit 50 can consist of a computer.

The control unit 50 is operatively associated with the illuminator 11, the scanning means 17 and the acquisition means 27 and is capable of controlling operation thereof by generating suitable control signals.

To generate these control signals, the control unit 50 preferably executes suitable software instructions stored in one or more memory locations of the same control unit.

The control unit 50 can also be operatively associated with a human-machine interface 60 for entering manual commands or for the execution of configuration or programming operations.

According to the invention, the perimeter 500 further comprises:
- first projection means 30 adapted to project a first projection beam 3 to uniformly illuminate a portion 1101 of the retina;
- second projection means 41 adapted to project a second projection beam 4 to project on the retina 101 at least a fixation target;
- third projection means 42 adapted to project a third projection beam 5 to project on the retina 101 at least a light stimulus.

According to the invention, during the operation of the scanning perimeter 500:
- the first projection beam 3 passes through the pupil 102 at the separation region 102D comprised between the first crossing region 102A, at which the illumination beam 1 passes through the pupil, and the second crossing region of the pupil 102B, at which the beam 2 of light reflected by the retina passes through the pupil;
- the second projection beam 4 passes through the pupil 102 at the first crossing region 102A or at the second crossing region 102B;
- the third projection beam 5 passes through the pupil 102 at the first crossing region 102A or at the second crossing region 102B.

The control unit 50 is operatively associated with the projection means 30, 41, 42 and is capable of controlling operation thereof by generating suitable control signals.

Preferably, the first projection means comprise one or more first emitters 301, 302.

Preferably, the emitters 301, 302 can be activated by the control unit 50 separately from each other.

Preferably, the first emitters 301, 302 comprise at least an LED.

Preferably, the first emitters 301, 302 comprise a plurality of LEDs capable of emitting light with different spectral bands.

The aforesaid first emitters can comprise one or more white LEDs 301, for example to project a white light background during a first type of perimetry test that uses white stimuli on a white background.

The aforesaid first emitters can also comprise one or more LEDs 302 capable of emitting colored light with various wavelengths, in particular yellow LEDs, for example to project a yellow light background, during a second type of perimetry test that uses blue stimuli on a yellow background.

Figure 8:
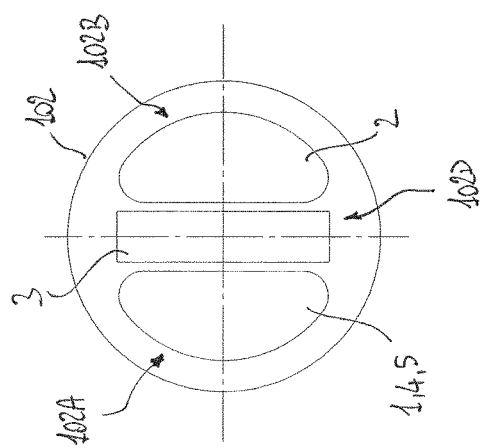
FIG. 8 schematically shows some details of the scanning perimeter of FIG. 6.

As indicated above, during the operation of the perimeter 500, the first projection beam 3 passes through the pupil 102 at the separation region 102D positioned between the crossing regions 102A, 102B of the illumination beam 1 and of the beam 2 of light reflected by the retina, respectively (FIG. 2, view 2A or FIG. 8).

This peculiarity of the perimeter 500 offers the possibility of generating the projection beam 3 in a region optically conjugated with the pupil 102 and comprised between the light beams 1, 2, advantageously without interfering with these latter.

Preferably, the first projection means 30 are operatively positioned in a first region of the perimeter 500 located between the illumination beam 1 and the beam 2 of light reflected by the retina, in proximity of a surface 102C conjugated with the pupil 102 (FIG. 1 and FIG. 2, view 2B).

The positioning of the projection means 30 in a region proximate to a conjugate 102C of the pupil 102 (during the operation of the perimeter 500) allows the first projection means 30 to project a projection beam 3 capable of uniformly illuminating the whole portion 1011 of retina being examined.

The first projection means 30 can be positioned in the same region in which the first separation means 16 of the light beams are located, in particular in a region proximate to the separation diaphragm 161.

Preferably, the first projection means 30 are positioned in a region comprised between the separation means 16 of the light beams and the scanning means 17.

A preferred region for operational assembly of the first projection means 30 is located in proximity of the diaphragm 161 between the illumination beam 1 and the beam 2 of light reflected by the retina, as shown in FIG. 1 and in FIG. 2, view 2B.

From this region, the first projection means 30 project the beam of light 3 toward the scanning means 17 that reflect it toward the optics 18.

The first projection means 30 advantageously generate a light beam 3 sufficiently wide (in angular direction) to cover the whole of the surface of the optics 18 in any moment of the optical scan implemented by the scanning means 17.

In this way, the projection beam 3 constantly covers the surface of the optics 18, preferably uniformly.

The projection beam 3, passing through the optics 18, continues in the direction D3 and passes through the eyepiece 19 that concentrates it in the separation region 102D, at which the projection beam 3 passes through the pupil 102.

Downstream of the crossing region 102D, the projection beam 3 continues diverging, expanding increasingly until it illuminates the whole portion 1011 of the retina being examined.

In this way, it is possible to produce the uniform light background required to perform the perimetry test, in a simple manner and above all without interfering with the optical paths of the illumination beam 1 and of the beam 2 of light reflected by the retina and used to acquire images of the retina.

The first projection means 30 could comprise a first projection mask (not shown) comprising one or more openings operatively associated with the first emitters 301, 302.

In principle, the second and third projection means can be positioned at two different regions of the perimeter 500.

Figure 3:
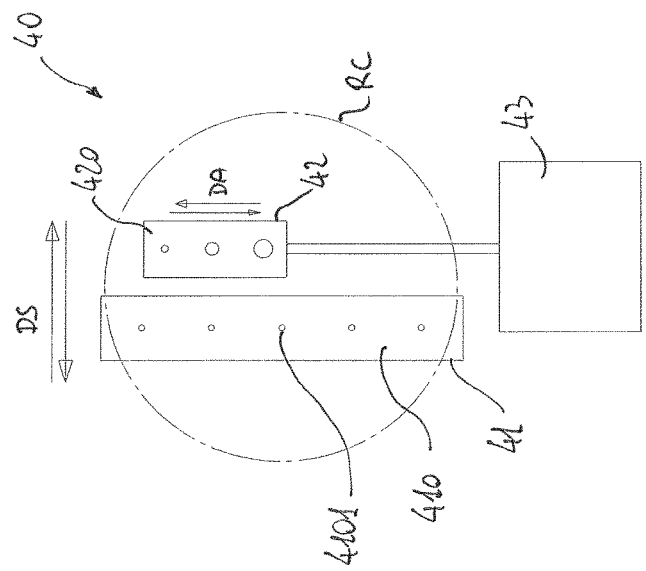
Figure 9:
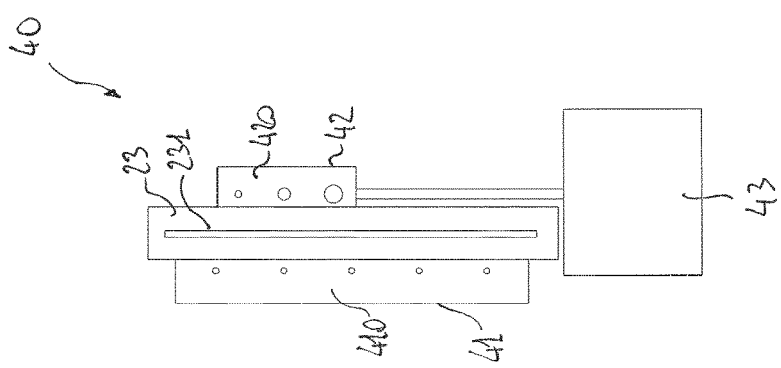
FIG. 9 schematically shows some details of the scanning perimeter of FIG. 7.

Alternatively, they can be integrated in a same projection unit 40 (see, for example, FIGS. 3, 9).

In the embodiment shown in FIG. 1, the scanning perimeter 500 comprises a beam splitter 22B to insert the projection beams 4, 5 into the optical acquisition path 2A. Through the beam splitter 22B, the projection means 41, 42 project the related projection beams 4, 5 in the direction D4 until reaching the retina 101.

The light beams 4, 5 pass through the pupil 102 at the same crossing region 102B passed through by the beam 2 of light reflected by the retina exiting from the eye 100, as shown in FIG. 1 and FIG. 2, view 2A.

Preferably, the second projection means 41 comprise one or more second emitters 411 and a second projection mask 410 provided with one or more second openings 4101 operatively associated with the emitters 411.

Preferably, the emitters 411 can be activated by the control unit 50 separately from one another.

The openings 4101 of the projection mask 410 allow a portion of the light emitted by the emitters 411 to be projected toward the retina 101.

Preferably, at least the projection mask 410 is positioned in a second region of the perimeter 500 substantially conjugated with the retina 101, during the operation of the same perimeter.

In this way, the image of the openings 4101 backlit by the emitters 411 can be focused on the retina 101.

Preferably, the third projection means 42 comprise one or more third emitters 421, 422, 423 and a third projection mask 420 provided with one or more third openings 4201, 4202, 4203 operatively associated with the third emitters 421, 422, 423.

Preferably, the emitters 421, 422, 423 can be activated by the control unit 50 separately from one another.

Preferably, the third projection means 42 can be moved reversibly along a direction DA substantially perpendicular to the scanning direction DS along which the scanning means 17 move the illumination beam 1 on the retina.

Figure 5:
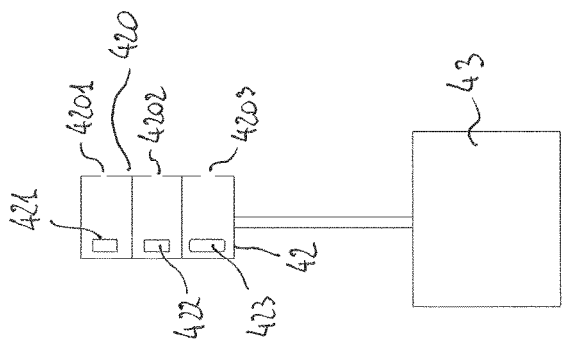

FIGS. 3, 5, 9 show a solution according to which the movement of the third projection means 42 is of translatory type.

The movement of the projection means 42 can also be of different type.

For example, the projection means 42 can perform a movement on an arc of circle (variant not shown). In this case the direction DA would be a direction tangent to said arc of circle.

Preferably, the perimeter 500 comprises an actuator 43 (advantageously controlled by the control unit 50) to selectively adjust the position of the third projection means 42.

Preferably, at least the projection mask 420 is positioned in the second region of the perimeter 500 substantially conjugated with the retina 101, during the operation of the same perimeter.

In this way, the image of the openings 4201 backlit by the emitters 421 can be focused on the retina 101.

Preferably, the third emitters 421, 422, 423 comprise at least an LED.

Preferably, the third emitters 421, 422, 423 comprise a plurality of LEDs capable of emitting light with different spectral bands.

Preferably, the third emitters 421, 422, 423 comprise at least a white LED.

Preferably, the third emitters 421, 422, 423 comprise at least a blue LED.

Preferably, the projection mask 420 comprises a plurality of third openings 4201, 4202, 4203 having different dimensions from one another.

With reference to FIG. 5, the emitters 421, 422 could consist of white LEDs and the corresponding openings 4201, 4202 can consist of circular holes having different diameters.

In this way, it is possible to project on the retina white light stimuli with different diameters, for example during a perimetry test with white light stimuli projected on a white light background.

The emitter 423 can consist of a blue LED adapted to project through the corresponding opening 4203 blue light stimuli on the retina, for example during a perimetry test with blue light stimuli projected on a yellow light background.

Preferably, the scanning means 17 are adapted to cyclically move the second projection beam 4 and the third projection beam 5, projected respectively by the second projection means 41 and by the third projection means 42, on the surface of the retina 101, along the scanning direction DS.

Preferably, the second and third projection means 41, 42 are adapted to project the second and third projection beam 4, 5 as light pulses of short duration, in a manner synchronized with the movements of the scanning means 17.

The second and third projection means 41, 42 can be activated by the control unit 50 with a certain activation frequency, preferably adjustable.

Preferably, the activation frequency of the second and third projection means 41, 42 is equal to the scanning frequency 1/TS of the scanning means 17 or equal to double the scanning frequency 1/TS or less than the scanning frequency 1/TS.

FIG. 3 schematically shows the optical conjugate of the retina RC at the assembly region of the masks 410, 420.

The projection beam 4 emitted by the second projection means 41 is scanned by the scanning means 17 before reaching the retina 101.

Consequently, the light image of the openings 4101 describes on the retina 101 a linear movement from one side to the other of the portion of retina 1011 being examined. In this way, each of the emitters 411 can project light on a linear band of retina oriented according to the scanning direction DS set by the scanning means 17.

To project a fixation target on the retina 101, in a given position of the field of view, the control unit 50 selects the emitter 411 corresponding to the position of the fixation target desired and cyclically activates the emitter 411 thus selected, in a manner synchronized with the cyclical movements of the scanning means 17.

The emitter 411 is activated for very brief time intervals DT in relation to the scanning period TS and is maintained deactivated for the rest of the scanning period TS.

Within the scope of the present invention, it is intended that the time intervals DT are very brief in relation to the scanning period TS if their duration is less than TS/50.

This solution allows a reduction, within acceptable limits, of the blur caused by movement of the fixation target on the retina as a result of the movement of the projection beam 4 set by the scanning means 17 during the activation period DT.

Given the short duration of the light pulse projected, the patient's eye perceives an illuminated region only slightly elongated in the scanning direction, therefore with a shape substantially similar to the image of the opening 4101 of the mask 410.

Advantageously, the start of the activation interval DT is delayed with respect to the end-of-travel moment of the scanning means 17 with a time delay corresponding to the position desired for the fixation target.

This delay defines the position of the fixation target along the linear region of retina scanned by the image of the opening 4101 corresponding to the emitter 411 selected.

By selecting this delay appropriately, it is possible to project fixation targets in random positions along the linear regions of retina scanned by the images of the openings 4101.

The projection of a fixation target can be obtained by projecting light pulses of duration DT cyclically, with an activation frequency of the emitter 411 equal to the scanning frequency 1/TS of the scanning means 17.

If the activation frequency with which the fixation target is projected is sufficiently high, for example above around 25 Hz, the eye perceives a continuous fixation target.

It is possible to project the fixation target with activation frequency double the scanning frequency 1/TS.

In this case, activation of the emitter 411 takes place both during the forward movements and during the return movements (along the scanning direction DS) of the scanning means 17.

It is advantageous to use different delays for the forward and return movements so that the fixation target on the retina is always projected at the same position.

The projection of the fixation target with activation frequency of the emitter 411 double the scanning frequency 1/TS has the advantage of allowing the patient to perceive a continuous fixation target also for a relatively low scanning frequency 1/TS.

It is also possible to project the fixation target with a lower activation frequency with respect to the scanning frequency 1/TS, in the case in which this latter is sufficiently high.

In this way, the light intensity of the fixation target can advantageously be reduced, adjusting the activation frequency of the emitter 411 and without adjusting its supply current.

During the test, the patient looks at the fixation target projected on his/her retina, with the aim of maintaining the eye still and oriented in the selected direction corresponding to the type of test performed.

For example, during a perimetry test, it is advantageous for the fixation target to be projected in central position, corresponding to the optical axis of the same perimeter.

Instead, to acquire the image of a lateral region of the retina, for example, it is advantageous for the fixation target to be projected in a lateral position.

Projection of the light stimuli by means of the third projection means 42 takes place substantially using the same method as projection of the fixation targets by the projection means 41.

To project a light stimulus on the retina 101, in a given position, the control unit 50:

selects the emitter 421 corresponding to the type of light stimulus desired (color or diameter of the stimulus);

controls the actuator 43 to move the third projection means 42 in a position in which the emitter 421 selected can project light on the retina in a band corresponding to the desired position of the stimulus;

cyclically activates the emitter 421 selected, in a manner synchronized with the cyclical movements of the scanning means 17.

The start of the activation interval of the emitter 421 is advantageously delayed with respect to the end-of-travel moments of the scanning means 17 with a delay corresponding to the position desired for the light stimulus.

The emitter 421 is activated for very short time intervals in relation to the scanning period T and is maintained deactivated for the rest of the scanning period TS.

Also in this case, the activation intervals of the emitter are lower than TS/50.

The light stimuli can be projected using an activation frequency of the projection means 42 equal to, double or lower than the scanning frequency 1/TS, in a very similar manner to the one used for projection of the fixation target by the projection means 41.

Figure 6:
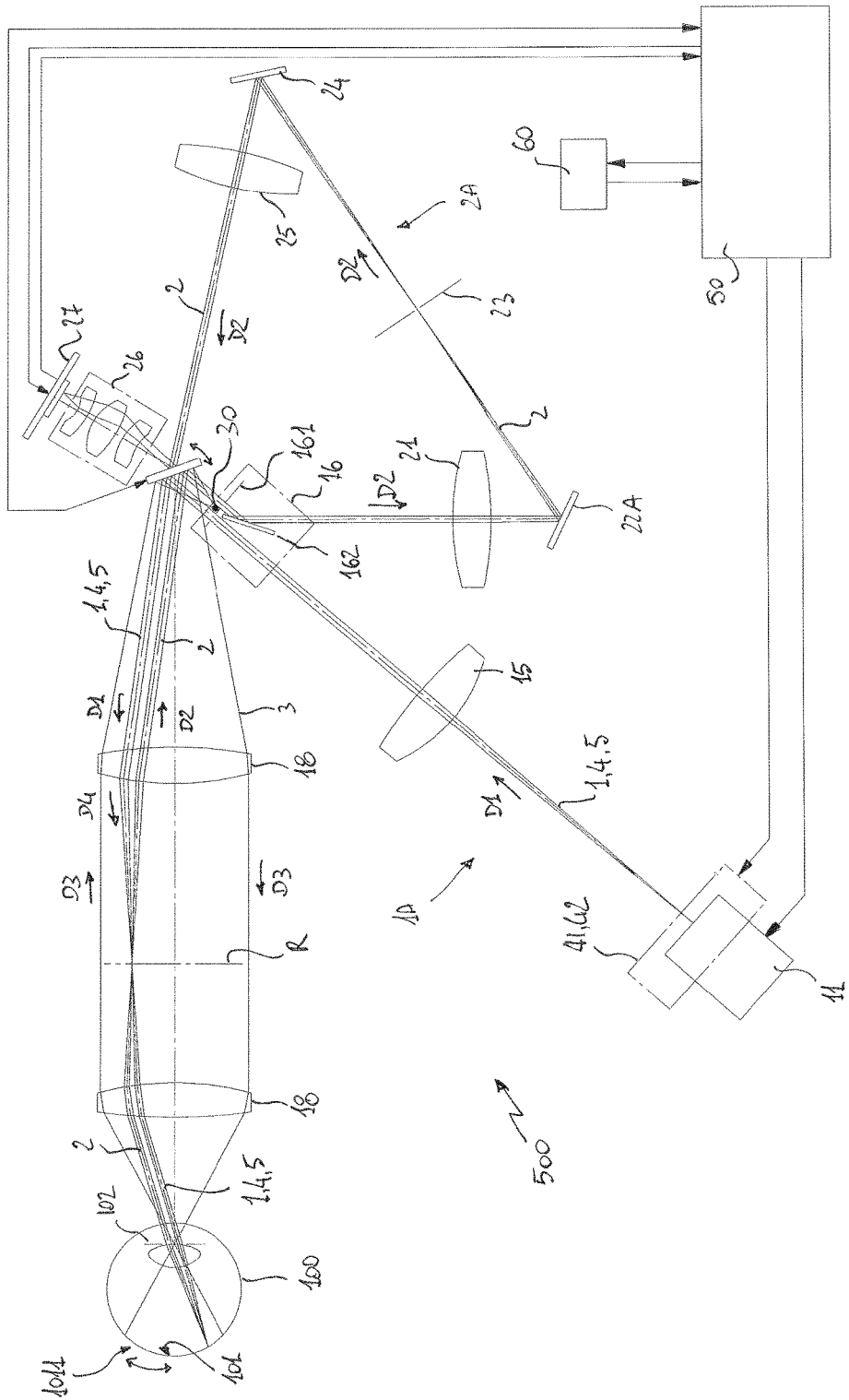
FIG. 6 schematically shows the scanning perimeter according to the invention, in a further embodiment thereof.

A further embodiment of the scanning perimeter 500 is shown in FIG. 6.

In this case, the second and third projection means 41, 42 are positioned in proximity of the illuminator 11.

In particular, the second and third projection mask 410, 420 are positioned in a third region of the perimeter 500 in proximity of the illuminator 11. This region is optically conjugated with the retina, during the operation of the same perimeter.

According to this embodiment, the projection means 41 and 42 are coupled to the optical illumination path 1A of the perimeter 500 and not to the optical acquisition path 2A, as occurs for the embodiment of FIG. 1.

Therefore, the projection means 41, 42 project the light beams 4, 5 that generate the fixation target and the light stimuli along the illumination path 1A.

The projection means 41, 42 project the related projection beams 4, 5 in the direction D4 until they reach the retina 101.

The light beams 4, 5 pass through the pupil 102 at the same crossing region 102A passed through by the illumination beam 1 entering the eye 100, as shown in FIG. 8.

According to the embodiment of FIG. 6, the beam splitter 22B can advantageously be replaced by a mirror 22A.

Preferably, the projection means 41 and 42 are positioned on one side and on the other of the exit of the illumination beam 1A from the illuminator 11.

In further structural and functional aspects thereof, the embodiment of FIG. 6 is very similar to the embodiment of FIG. 1, described above.

Figure 7:
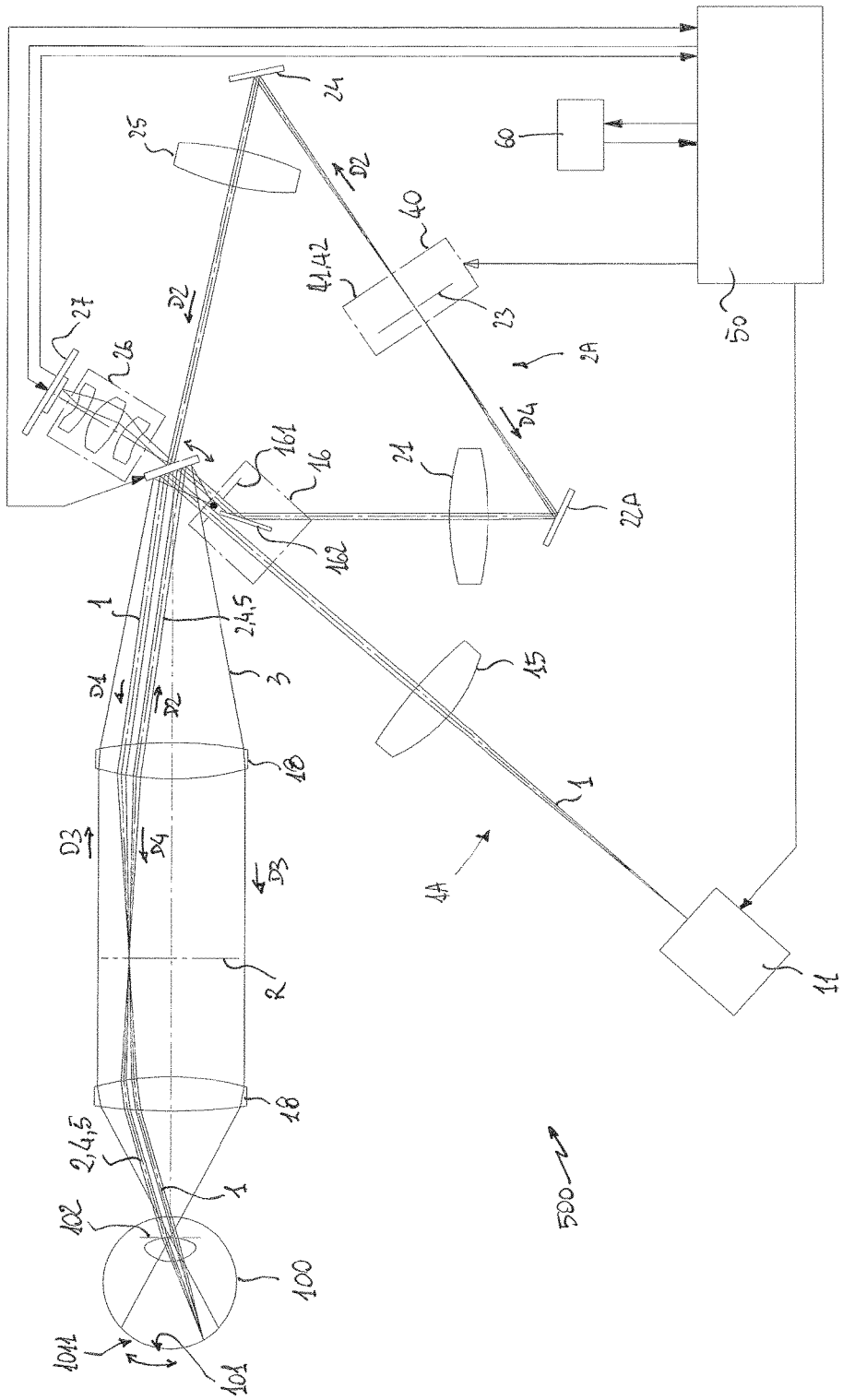
FIG. 7 schematically shows the scanning perimeter according to the invention, in an embodiment thereof.

A further embodiment of the scanning perimeter 500 is shown in FIG. 7.

In this case, the second and third projection means 41, 42 are positioned in proximity of the confocal diaphragm 23.

In particular, the second and third projection mask 410, 420 are positioned in a fourth region of the perimeter 500 in proximity of the confocal diaphragm 23. This region is optically conjugated with the retina, during the operation of the same perimeter.

The projection means 41, 42 project the related projection beams 4, 5 in the direction D4 until reaching the retina 101.

The light beams 4, 5 pass through the pupil 102 at the same crossing region 102B passed through by the beam 2 of light reflected by the retina exiting from the eye 100, as shown in FIG. 2, view 2A.

According to the embodiment of FIG. 7, the beam splitter 22B can advantageously be replaced by a mirror 22A.

A possible solution for integration of the confocal diaphragm 23 in an assembly that also comprises the second and the third projection means 41 and 42 is shown in FIG. 9.

Figure 4:
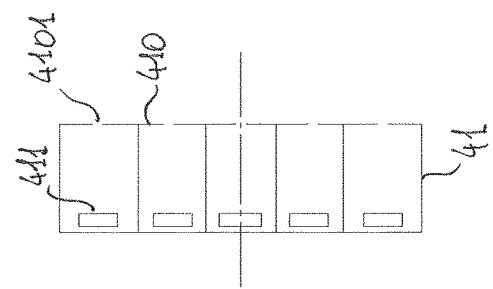

The construction of the second and third projection means 41, 42 is substantially the same as described above, in relation to FIGS. 3-5.

The confocal diaphragm 23 is positioned in a region conjugated with the retina 101 of the eye 100, in proximity of the surfaces of the masks 410 and 420, preferably above these, as shown in FIG. 9.

The beam of light 2 reflected by the retina passes through the confocal opening 231 and between the second projection means 41 and the third projection means 42, to end on the acquisition means 27 that acquire the image of the retina.

In further structural and functional aspects thereof, the embodiment of FIG. 7 is very similar to the embodiment of FIG. 1, described above.

The operating positions of the second projection means 41 and of the third projection means 42 must not be intended as limited to the solutions shown in relation to FIGS. 1-10, described above, according to which the projection means 41, 42 are positioned at a same region of the perimeter 500.

According to further embodiments (not shown), the projection means 41, 42 could be positioned at two different regions of the perimeter 500.

For example, the second projection means 41 could be positioned in proximity of the illuminator 11 while the third projection means 42 could be positioned in proximity of the confocal diaphragm 23.

The choice of the operating positions of the projection means 41 and 42 can be dictated by reasons of simplicity of construction or by the need to reduce industrial costs.

Figure 11:
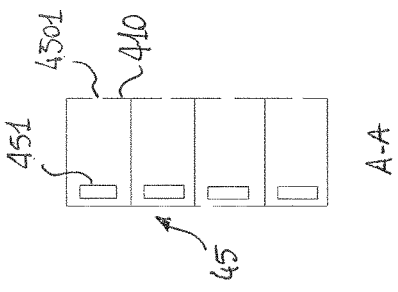
FIGS. 10-11 schematically show some details of the scanning perimeter of FIG. 1, in a further variant of embodiment thereof.
Figure 10:
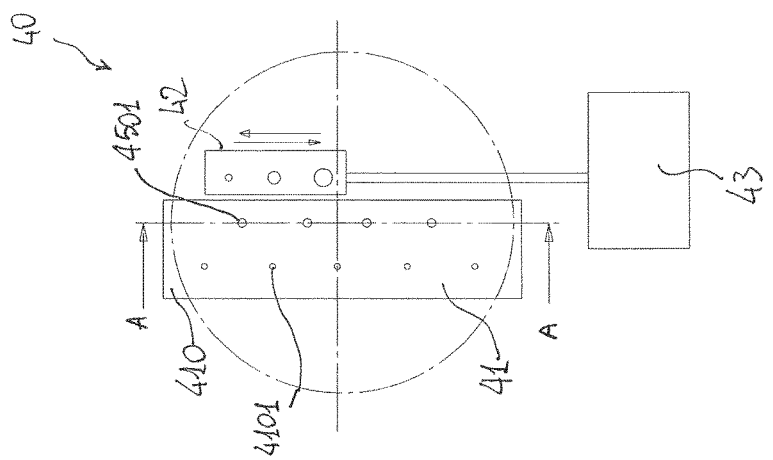

FIGS. 10-11 schematically show a further variant of the embodiment shown in FIG. 1.

According to this variant of embodiment, the perimeter 500 comprises detection means 45 of the light comprising one or more photosensitive elements 451 adapted to provide detection signals indicative of the light power received.

The detection means 45 can be integrated with the projection means 41, 42 in a single assembly 40.

Preferably, the photosensitive elements 451 are operatively associated with the second projection mask 410, which, in this case, comprises fourth openings 4501 for the passage of light toward the photosensitive elements 451.

Preferably, the openings 4501 are positioned in a row, according to a direction conjugated with the direction of a line of light projected by the illuminator 11 on the retina during the operation of the perimeter 500.

This ensures a good transfer of light power reflected by the linear region of illuminated retina to the photosensitive elements 451.

According to alternative solutions, the detection means 45 could comprise a fourth mask different from the mask 410 and provided with one or more openings 4501, preferably arranged as already indicated.

The detection means 45 of the light advantageously allow measurement of the quantity of reflected light that returns from the retina toward the acquisition means 27 during the filming of images of the retina.

The control unit 50 can thus control the illuminator 11 to perform automatic adjustment of the exposure of the acquisition means 27.

In this way, during acquisition of images of the retina, the acquisition means 27 can advantageously be exposed to a same quantity of light, also with retinas having different reflectivities.

A preferred method for operating the scanning perimeter 500 is briefly described below. This operating method advantageously comprises the following steps (also in a different order to the one indicated below):

activating the second projection means 41 to project a fixation target in a desired position;
activating the illuminator 11;
acquiring a live video image of the retina through the acquisition means 27;
making any adjustments of the perimeter 500, for example focusing of the retina on the acquisition means 27;
activating the first projection means 30 to uniformly illuminate a portion 1101 of retina 101;
activating the third projection means 42 to project light stimuli on the retina;
during activation of the third projection means 42, analyzing the live video image of the retina, detecting any movements of the eye and correcting the position of the light stimuli projected by the projection means 42 based on any movements of the eye detected;
acquiring, through the acquisition means 27, images of the retina obtained projecting an infrared, white or colored light on the retina by means of the illuminator 11.

The perimeter 500 according to the invention has considerable advantages with respect to the prior art.

Positioning of the projection beams 3, 4, 5 at the regions 102D, 102A, 102B of the pupil makes it possible to:

project a uniform light background, a fixation target and light stimuli on the retina without interfering substantially with the optical paths 1A, 2A of the illumination beam 1 and of the light 2 reflected by the retina, thus maintaining the quality of the images acquired substantially the same;
reduce the overall dimensions and industrial production cost of the projection means 30, 41, 42;
reduce the weight and overall dimensions of the perimeter 500.

The particular operational assembly of the first projection means 30 makes it possible to:

obtain a good uniformity of the light background projected on the retina;
project, in a simple and inexpensive manner, constant light backgrounds of various colors;
maintain a good uniformity of the light background projected on the retina also in the presence of defects of the projection means 30 or of the any dirt deposited on the projection means 30 during assembly;
obtain considerable simplicity of construction and a substantial reduction in industrial costs.

The particular activation method of the projection means 41, 42 described above make it possible to:

use reliable and inexpensive electronic means (control unit 50) to manage positioning of the fixation target and of the light stimuli instead of more costly and less accurate electromechanical means;
project a larger number of fixation targets and light stimuli than the number of emitters used for the projection means 41, 42;
continuously adjust, according to the scanning direction DS, the positions in which the fixation targets and the light stimuli can be projected.

The use of the light detection means 45 makes it possible to produce, in a simple and inexpensive manner, an integrated assembly that projects fixation targets and light stimuli on the retina and that measures the quantity of light reflected by the retina to adjust the exposure of the acquisition means 27 during the acquisition of images.

The operating positioning of the projection means 41, 42, at the illuminator 11 or the confocal diaphragm 23, makes it possible not to interfere with the optical paths 1A, 2A and not to cause losses to the light beam 2 used to acquire images of the retina, and therefore to maintain the same quality of the images acquired.

The use of projection means 41, 42 provided with masks and emitters makes it possible to obtain a good visual quality of the fixation targets or of the light stimuli, with respect to conventional solutions that use LCD displays.

The use of projection means 42 with a plurality of emitters, optionally of different colors and with mask with a plurality of openings, optionally different from one another, makes it possible to simply project light stimuli with different dimensions and colors, depending on the requirements of the different types of tests to be conducted.

The use of LEDs in the projection means 30, 41, 42 makes it possible to obtain a high stability of the light power projected (with respect to the temperature and to aging of the machine) and a wide design choice with regard to the power, colors and dimensions of the emitters.

The emitters consisting of LEDs are also characterized by limited dimensions and reduced industrial costs.

The projection of the light stimuli with automatic compensation of the movements of the eye improves the measurement precision of the visual function of the eye.

The scanning perimeter 500 has a very compact structure and is easy to produce on an industrial scale, with considerable advantages in terms of limiting production costs.

The invention claimed is:

1. A scanning perimeter comprising:
   an illuminator adapted to project an illumination beam to illuminate the retina of an eye, said illumination beam passing through the pupil of the eye at a first crossing region during an operation of said scanning perimeter;
   acquisition means adapted to receive beam of light reflected by the retina and to acquire images of the retina;
   scanning means adapted to move said illumination beam on the surface of the retina along a scanning direction and with a scanning period;
   separation means of the light beams adapted to define a second crossing at the pupil during the operation of said scanning perimeter, at which the beam of light reflected by the retina and used by said acquisition means to acquire images of the retina passes through the pupil, said second crossing region being spatially separated from said first crossing region;
   a control unit to control the operation of said scanning perimeter;
   first projection means adapted to project a first projection beam to illuminate a portion of retina, said first projection beam passing through the pupil at a separation region comprised between said first crossing region of the pupil and said second crossing region of the pupil, during the operation of said scanning perimeter;
   second projection means adapted to project a second projection beam to project at least a fixation target on the retina, said second projection beam passing through the pupil at said first crossing region or at said second crossing region, during the operation of said scanning perimeter;
   third projection means adapted to project a third projection beam to project at least a light stimulus on the retina, said third projection beam passing through the pupil at said first crossing region or at said second crossing region, during the operation of said scanning perimeter.

2. The scanning perimeter of claim 1, wherein the first projection means are positioned in a first region of said scanning perimeter positioned between said illumination beam and said beam of light reflected by the retina, at said separation means of the light beams or between said separation means of the light beams and said scanning means.

3. The scanning perimeter of claim 1, wherein said scanning means cyclically move said second projection beam and said third projection beam on the surface of the retina along said scanning direction, during the operation of said scanning perimeter.

4. The scanning perimeter of claim 3, wherein said second and third projection means project said second and third projection beam during time intervals having a shorter duration than a fiftieth of said scanning period, during the operation of said scanning perimeter.

5. The scanning perimeter of claim 3, wherein said second and third projection means project said second and third projection beam in a manner synchronized with the movements of said scanning means, during the operation of said scanning perimeter.

6. The scanning perimeter of claim 5, wherein during the operation of said scanning perimeter, said second and third projection means are activated with:
   an activation frequency equal to the scanning frequency of said scanning means;
   an activation frequency equal to double the scanning frequency of said scanning means; or
   an activation frequency lower than the scanning frequency of said scanning means.

7. The scanning perimeter of claim 1, wherein said first projection means comprise at least one LED.

8. The scanning perimeter of claim 7, wherein said first emitters comprise at least two LEDs capable of emitting light with different spectral bands.

9. The scanning perimeter of claim 8, wherein said first emitters comprise one or more of a white LED and a yellow LED.

10. The scanning perimeter of claim 1, wherein said second projection means comprise one or more second emitters and a second projection mask provided with one or more second openings; and
    said third projection means comprise one or more third emitters and a third projection mask provided with one or more third openings.

11. The scanning perimeter of claim 10, wherein the third projection means are reversibly movable according to a direction substantially perpendicular to said scanning direction.

12. The scanning perimeter of claim 10, wherein at least one of said second and third projection masks is positioned in a second region of said scanning perimeter optically conjugated with the retina, during the operation of said scanning perimeter, said scanning perimeter comprising a beam splitter to insert said second and third projection beams in an optical acquisition path of said scanning perimeter.

13. The scanning perimeter of claim 10, wherein at least one of said second and third projection masks is positioned in a third region of said scanning perimeter in proximity of said illuminator, said third region being optically conjugated with the retina during the operation of said scanning perimeter.

14. The scanning perimeter of claim 10, wherein at least one of said second and third projection masks is positioned in a fourth region of said scanning perimeter in proximity of a confocal diaphragm of said scanning perimeter, said fourth region being optically conjugated with the retina during the operation of said scanning perimeter.

15. The scanning perimeter of claim 10, wherein said third projection mask comprises a plurality of third openings having different dimensions from one another.

16. The scanning perimeter of claim 10, wherein said third emitters comprise at least a LED.

17. The scanning perimeter of claim 16, wherein said third emitters comprise at least two LEDs capable of emitting light with different spectral bands.

18. The scanning perimeter of claim 17, wherein said third emitters comprise one or more of a white LED and a blue LED.

19. The scanning perimeter of claim 1, comprising light detection means comprising one or more photosensitive elements adapted to provide detection signals indicative of the received light power.

20. The scanning perimeter of claim 19, wherein said one or more photosensitive elements are operatively associated with said second projection mask, said second projection mask comprising fourth openings for the passage of light toward said photosensitive elements.

21. A method to operate a scanning perimeter comprising an illuminator, a first projection means, a second projection means, and a third projection means, the method comprising:
- activating the second projection means to project a fixation target in a desired position;
- activating the illuminator to project an illumination beam to illuminate a retina of an eye, said illumination beam passing through a pupil of the eye at a first crossing region;
- acquiring live video images of the retina;
- making any adjustments of said scanning perimeter;
- activating said first projection means to uniformly illuminate a portion of the retina;
- activating said third projection means to project light stimuli on the retina;
- during the activation of said third projection means, analyzing the live video images of the retina, detecting any movements of the eye, and correcting the position of said light stimuli based on any detected movements of the eye; and
- acquiring images of the retina by projecting a white light, an infrared light or a colored light on the retina via said illuminator.

22. A scanning perimeter comprising:
- a light source adapted to project an illumination beam to illuminate a retina of an eye, said illumination beam passing through a pupil of the eye at a first crossing region during an operation of said scanning perimeter;
- one or more sensors of a video camera adapted to receive beam of light reflected by the retina and to acquire images of the retina;
- a resonant mirror oscillating around a rotation axis and adapted to move said illumination beam on the surface of the retina along a scanning direction and with a scanning period;
- a separation diaphragm adapted to define a second crossing region at the pupil during the operation of said scanning perimeter, at which the beam of light reflected by the retina and used by said one or more sensors to acquire images of the retina passes through the pupil, said second crossing region being spatially separated from said first crossing region;
- a control unit to control operation of said scanning perimeter;
- one or more first emitters activated by the control unit to project a first projection beam to illuminate a portion of retina, said first projection beam passing through the pupil at a separation region comprised between said first crossing region of the pupil and said second crossing region of the pupil, during the operation of said scanning perimeter;
- one or more second emitters activated by the control unit to project a second projection beam to project at least a fixation target on the retina, said second projection beam passing through the pupil at said first crossing region or at said second crossing region, during the operation of said scanning perimeter;
- one or more third emitters activated by the control unit to project a third projection beam to project at least a light stimulus on the retina, said third projection beam passing through the pupil at said first crossing region or at said second crossing region, during the operation of said scanning perimeter.

* * * * *